(12) United States Patent
Marler et al.

(10) Patent No.: US 7,347,203 B2
(45) Date of Patent: Mar. 25, 2008

(54) HEAT AND MOISTURE FILTER EXCHANGER AND METHOD

(75) Inventors: Gregory S. Marler, Tucson, AZ (US); David T. Sladek, Tucson, AZ (US)

(73) Assignee: Thayer Medical Corporation, Tucson, AZ (US)

( * ) Notice: Subject to any disclaimer, the term of this patent is extended or adjusted under 35 U.S.C. 154(b) by 0 days.

(21) Appl. No.: 10/654,797

(22) Filed: Sep. 4, 2003

(65) Prior Publication Data
US 2004/0123974 A1 Jul. 1, 2004

Related U.S. Application Data

(60) Provisional application No. 60/411,213, filed on Sep. 16, 2002.

(51) Int. Cl.
*A62B 18/08* (2006.01)

(52) U.S. Cl. .............. 128/201.13; 128/200.14; 128/200.23; 128/203.17; 128/203.22; 128/203.26; 128/203.27; 128/204.17; 128/205.24; 128/909; 128/911; 128/912; 165/119

(58) Field of Classification Search ............ 128/200.14, 128/200.23, 201.13, 203.17, 203.22, 203.26, 128/203.27, 204.17, 205.24, 909, 911, 912; 165/119
See application file for complete search history.

(56) References Cited

U.S. PATENT DOCUMENTS

| | | | | |
|---|---|---|---|---|
| 4,016,878 A | * | 4/1977 | Castel et al. ............ | 128/202.26 |
| 4,090,513 A | * | 5/1978 | Togawa ................. | 128/201.13 |
| 4,318,398 A | * | 3/1982 | Oetjen et al. ........... | 128/201.13 |
| 4,327,717 A | * | 5/1982 | Oetjen et al. ........... | 128/201.13 |
| 4,621,632 A | * | 11/1986 | Bartels et al. .......... | 128/203.27 |
| 4,771,770 A | * | 9/1988 | Artemenko et al. ..... | 128/201.13 |
| D301,377 S | * | 5/1989 | Lambert .................. | D24/164 |
| 5,005,569 A | * | 4/1991 | Pasternack ............. | 128/204.13 |
| 5,022,394 A | * | 6/1991 | Chmielinski ........... | 128/207.14 |
| 5,460,172 A | * | 10/1995 | Eckerbom et al. ...... | 128/201.13 |
| 5,462,048 A | * | 10/1995 | Lambert et al. ........ | 128/201.13 |
| 5,577,494 A | * | 11/1996 | Kuypers et al. ........ | 128/201.13 |
| 5,590,644 A | * | 1/1997 | Rosenkoetter ......... | 128/201.13 |
| 5,647,344 A | * | 7/1997 | Turnbull ................. | 128/201.13 |
| 5,906,201 A | * | 5/1999 | Nilson .................... | 128/203.16 |
| 5,992,413 A | * | 11/1999 | Martin et al. ........... | 128/201.13 |
| 6,588,421 B1 | * | 7/2003 | Diehl et al. ............. | 128/201.13 |
| 6,745,766 B2 | * | 6/2004 | Fini ........................ | 128/204.17 |

FOREIGN PATENT DOCUMENTS

| | | | |
|---|---|---|---|
| GB | 0 265 163 A2 | * | 4/1988 |
| GB | 0 409 402 A1 | * | 1/1991 |

* cited by examiner

*Primary Examiner*—Henry Bennett
*Assistant Examiner*—Nihir Patel
(74) *Attorney, Agent, or Firm*—Cahill, von Hellens & Glazer, P.L.C.

(57) ABSTRACT

A heat and moisture exchanger for both conducting a stream of air produced by a ventilator to a moisturizing medium and internally bypassing the moisturizing medium if aerosolized medication is introduced into the stream includes a housing having a ventilator-side port coupled to an outlet of a ventilator and a source of aerosolized medication. The housing has a patient-side port for coupling to a patient to provide ventilation including either air or air carrying aerosolized medication. A first path conducts air from the ventilator-side port through the moisturizing medium and the patient-side port, and a second path conducts air carrying aerosolized medication from the ventilator-side port directly to the patient-side port. A two-way valve mechanism in the housing selectively couples the ventilator-side port into fluid communication with one or the other of the first and second paths.

13 Claims, 5 Drawing Sheets

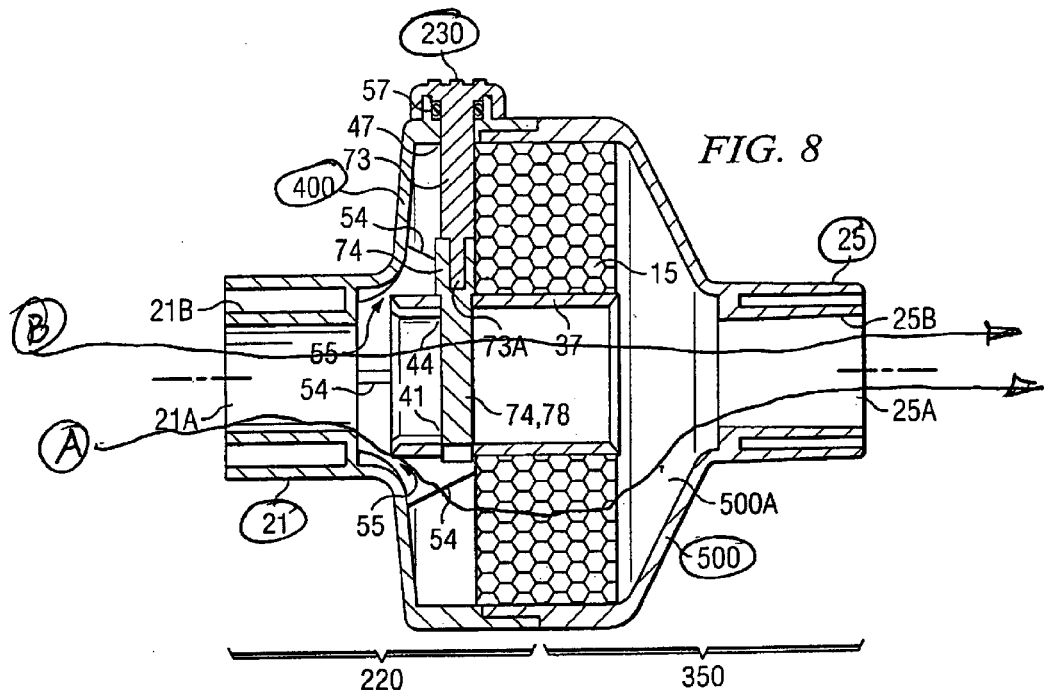
FIG. 8
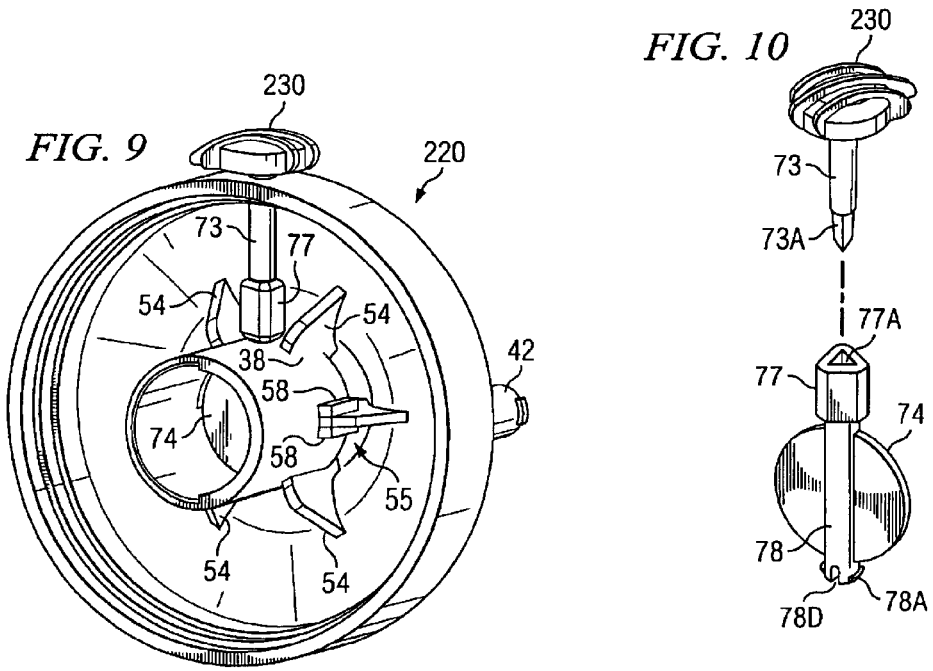
FIG. 9
FIG. 10

HEAT AND MOISTURE FILTER EXCHANGER AND METHOD

CROSS REFERENCE TO RELATED APPLICATION

This application claims the benefit of prior filed co-pending U.S. provisional application Ser. No. 60/411,213 filed Sep. 16, 2002, entitled "HEAT AND MOISTURE FILTER EXCHANGER AND METHOD" by Gregory S. Marler and David T. Sladek.

BACKGROUND OF THE INVENTION

The present invention relates generally to systems for respiratory therapy, particularly to ventilator systems that includes heat and moisture exchanger (HME) media or heat and moisture exchanger (HME) media in the respiratory path and also provides the additional capability of administering aerosol medication to a patient effectively without interrupting the respiratory path.

Figure 1:
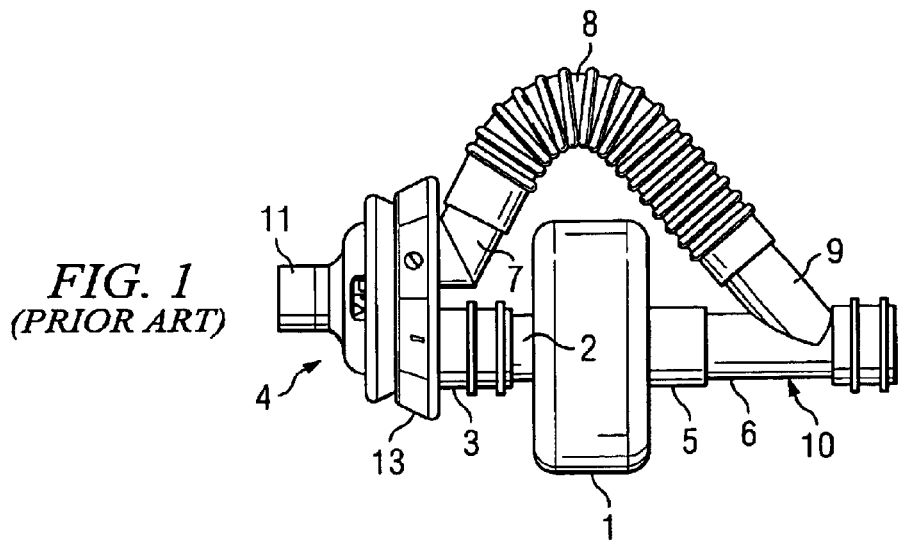

The closest prior art is believed to be illustrated in FIG. 1, in which a conventional heat and moisture exchanger (HME) 1 has a port 2 connected to a port 3 of a bypass device 4. Bypass device 4 is marketed by DHD Healthcare of Watsonville, N.Y. under the trademark CIRCUVENT. Heat and moisture exchanger 1 has a port 5 connected to port 6 of a Y connector having a connector which is coupled to an endotracheal tube (not shown) in the patient. Bypass device 4 includes another port 7 connected to one end of a flexible bypass tube 8 having its other end connected to another port 9 of Y connector 10. Bypass device 4 has a port 11 connected by suitable tube to a ventilator (not shown). A rotatable control ring 13 can be adjusted so that gas received through port 11 from the ventilator is selectively routed through either heat and moisture exchanger 1 or bypass tube 8. If aerosol medication is introduced into the respiratory path upstream from port 11, then control ring 13 is turned to direct the gas carrying the aerosol medication around heat and moisture exchanger 1 through bypass tube 8. This prevents the aerosol droplets/particles from impacting on the media of heat and moisture exchanger 1 (and any filter material that may be provided with it).

The bypass tube 8 of the assembly shown in FIG. 1 has a large volume of "dead space" which results in a relatively large amount of previously exhaled air being re-breathed by the patient. This reduces the amount of oxygen received by the patient's lungs and is always undesirable, and in some instances can be dangerous, especially for a critically ill infant being supported on a ventilator. The assembly shown FIG. 1 is bulky, relatively heavy, and tends to be leaky.

The cost of a typical HME or HMEF element 1 or an HCH element can be in the range from approximately $1.50 to $5.00, and the bypass device 4 can cost from approximately $3.50 to $7.00.

Thus, there is an unmet need for a device and method for selectively conducting a stream of air produced by a ventilator through a moisturizing medium in the device or internally bypassing the moisturizing medium to prevent aerosolized medication that has been introduced into the stream from contacting the moisturizing medium.

There also is an unmet need for such a device and method that reduces the cost of selectively conducting a stream of air produced by a ventilator through a moisturizing medium in the device or internally bypassing the moisturizing medium to prevent aerosolized medication that has been introduced into the stream from contacting the moisturizing medium.

There also is an unmet need for such a device and method that reduces the cost of selectively conducting a stream of air produced by a ventilator through a moisturizing medium in the device or internally bypassing the moisturizing medium to prevent aerosolized medication that has been introduced into the stream from contacting the moisturizing medium, wherein the device and method also reduce the risk of infection to the patient.

There also is an unmet need for such a device and method that reduces the cost of selectively conducting a stream of air produced by a ventilator through a moisturizing medium in the device or internally bypassing the moisturizing medium to prevent aerosolized medication that has been introduced into the stream from contacting the moisturizing medium, wherein the device and method also reduce the risk to the patient associated with a large volume of a "dead space" in the respiratory path.

SUMMARY OF THE INVENTION

It is an object of the present invention to provide a device and method that reduces the cost of selectively conducting a stream of air produced by a ventilator through a moisturizing medium in the device or internally bypassing the moisturizing medium to prevent aerosolized medication that has been introduced into the stream from contacting the moisturizing medium.

It is another object of the present invention to provide an improved unitary device and a method for selectively conducting a stream of air produced by a ventilator through a moisturizing medium in the device or internally bypassing the moisturizing medium to prevent aerosolized medication that has been introduced into the stream from contacting the moisturizing medium.

It is another object of the present invention to provide a device and method that reduces the cost of selectively conducting a stream of air produced by a ventilator through a moisturizing medium in the device or internally bypassing the moisturizing medium to prevent aerosolized medication that has been introduced into the stream from contacting the moisturizing medium and that also reduces the risk of infection to the patient.

It is another object of the invention to provide a device and method that reduces the cost of selectively conducting a stream of air produced by a ventilator through a moisturizing medium in the device or internally bypassing the moisturizing medium to prevent aerosolized medication that has been introduced into the stream from contacting the moisturizing medium and that also reduces the risk to the patient associated with a large volume of "dead space" in the respiratory path.

Briefly described, and in accordance with one embodiment, the present invention provides a heat and moisture exchanger for selectively conducting a stream of air produced by a ventilator through a moisturizing medium or internally bypassing the moisturizing medium if aerosolized medication is introduced into the stream, the device including a housing having a ventilator-side port coupled to a ventilator and a source of aerosolized medication, the housing also having a patient-side port coupled to a patient to provide ventilation including either air or air with aerosolized medication. A first path within the device conducts non-aerosolized air between the ventilator-side port and the patient-side port, and a second path conducts air carrying aerosolized medication between the ventilator-side port and the patient-side port. A two-way valve mechanism is included within the housing for selectively coupling the ventilator-side port into fluid communication with one or the other of the first and second paths.

In one embodiment, the heat and moisture exchanger includes a housing having a ventilator-side port (21) configured to be coupled to an outlet of a ventilator and a source of aerosolized medication, the housing also having a patient-side port (25) configured to be coupled to a patient to provide ventilation to the patient. The structure within the housing forms a first path for conducting non-aerosolized air from the ventilator-side port through the moisturizing medium to the patient-side port and a second path for conducting air carrying aerosolized medication from the ventilator-side port to the patient-side port by bypassing the moisturizing medium. The two-way valve mechanism in the housing selectively couples the ventilator-side port into fluid communication with one or the other of the first and second paths. An external valve control (230) extends through the housing to control the two-way valve mechanism. A tube (37) is supported between the ventilator-side port (21) and the patient-side port (25), wherein the second path extends entirely through the tube. The two-way valve mechanism selectively blocks or opens a portion of the second path extending through the tube (37) in response to the external valve control (230). The moisturizing medium (15) is disposed between an outer surface of the tube (37) and an inner surface of the housing. The first path extends around the tube and through the moisturizing medium. A gap (55) between a first end of the tube (37) and the ventilator-side port (21) forms part of the first path. The two-way valve mechanism includes a butterfly valve coupled to an actuator mechanism. The valve includes a valve disk 74 integral with a cylindrical valve post 78 having a female coupling element 77 at its upper end which mates with a the mail coupling device 73A. The actuator mechanism includes an actuation knob (73) external to ventilator-side housing 400, an actuator stem 73 extending through ventilator-side housing 400 and having the male coupling element 73A at its lower end. The moisturizing medium (15) is annular and is disposed around the tube (37), an inner surface of the moisturizing medium forming a seal with an outer surface of the tube, an outer surface of the moisturizing medium forming a seal with an inner surface of the housing. The housing is cylindrical, and wherein the inner surface and outer surface of the moisturizing medium are cylindrical. The ventilator-side section (220) includes a plurality of integral support members 54 which support the tube (37) in axial alignment between the ventilator-side port (21) and the patient-side port (25).

BRIEF DESCRIPTION OF THE DRAWINGS

FIG. 1 is a side elevation view of a prior art assembly including an HME device and a bypass unit.

FIG. 2 is a side elevation view of a HME/bypass unit according to the present invention.

FIG. 2A is a block diagram showing a connection of the HME/bypass unit of FIG. 2 in a ventilator circuit.

FIG. 3 is a longitudinal section view showing the interior of the HME/bypass unit of FIG. 2.

FIG. 4 is a perspective right upper view showing the interior of the ventilator-side section 22 of the HME/bypass unit of FIGS. 2 and 3.

FIG. 5 is a perspective left view showing the interior of the patient-side section 35 of the HME/bypass unit of FIGS. 2 and 3.

FIG. 6 is a perspective lower right view of the valve plate 23 of the HME/bypass unit of FIGS. 2 and 3.

FIG. 7 is an a front upper perspective view of another embodiment of a HME/bypass unit according to the present invention.

FIG. 8 is a longitudinal section view showing the interior of the HME/bypass unit of FIG. 7.

FIG. 9 is a perspective view showing the interior of the ventilator-side section of the HME/bypass unit of FIG. 7.

FIG. 10 is an elevation view of a butterfly valve assembly included in the ventilator-side section of the HME/bypass unit in FIG. 9.

DETAILED DESCRIPTION OF THE PREFERRED EMBODIMENTS

Referring to FIGS. 2, 2A and 3–6, an HME/bypass device 20 includes a ventilator-side section 22 having a ventilator-side port 21, and a patient-side section 35 having a patient-side port 25. A knurled, rotatable collar 23A of a valve plate 23 is used to control a 2-way valve located inside of a complete housing including both ventilator-side section 22 and patient-side section 35. The outer surface of ventilator-side port 21 is partially knurled, as shown. A CO2 monitoring port 42 is provided as an integral part of a ventilator-side section 22, and a drainage port 43 is provided as an integral part of patient-side section 35.

FIG. 2A shows a ventilating system 100 in which HME/bypass device 20 can be connected, wherein a ventilator 101 is coupled by suitable respiratory tubing to one port of an MDI (metered dose inhaler) injection device 103 having an opposite port connected by suitable respiratory tubing to ventilator-side port 21 of HME/bypass device 20. HME/bypass device 20 includes a patient-side port 25 which is connected to an endotracheal tube 107 that has been intubated into o the trachea of a patient.

The air pumped by ventilator 101 into ventilator-side port 21 does not carry any aerosolized medication unless an MDI canister 105 is inserted into MDI injection device 103 and depressed so as to open the valve of MDI canister 105. Knurled collar 23A is initially set to a position that causes air from ventilator 101 to pass through an optional annular bacterial and viral filter 48 disposed in ventilator side chamber 40A and through an annular HME element 15 in the patient side chamber 50A (as shown in FIG. 3) and then through patient-side port 25 and endotracheal tube 107 into the lungs of the patient. If it is desirable to administer aerosolized medication to the patient, then knurled collar 23A is rotated 90 degrees to a second position which causes air pumped by ventilator 101 to pass directly from ventilator-side port 21 through patient-side port 25 without passing through HME element 15 or the optional bacterial and viral filter element 48. Then, an MDI canister 105 containing the desired medication is inserted into an injection port of MDI injection device 103 and depressed so as to open a valve of MDI canister 105 and thereby cause a plume of medication droplets/particles to be sprayed into the air stream produced by ventilator 101. The plume of medication droplets/particles is carried directly through an unobstructed path through HME/bypass device 20 and endotracheal tube 107 into the lungs of the patient. This prevents medication droplets/particles from being deposited on HME element 15 or the optional bacterial and viral filter element 48. Alternatively, a device other than an MDI injection device 103, such as a liquid nebulizer, might be used to introduce aerosolized medication into the stream of air produced by ventilator 101.

Referring to FIGS. 3–6, ventilator-side port 21 of HME/bypass device 20 includes a cylindrical passage 21A that extends into an interior first chamber 40A bounded by a first chamber wall 40 that is integral with the cylindrical tube that forms/bounds passage 21A. A portion of passage 21A extends into first chamber 40A and forms a cylindrical left cage 30, the right end of which includes a narrow cylindrical section 31. Half of the right end of passage 21A is blocked by two sections of a circular disk 32, as shown in FIG. 4.

Figure 3:
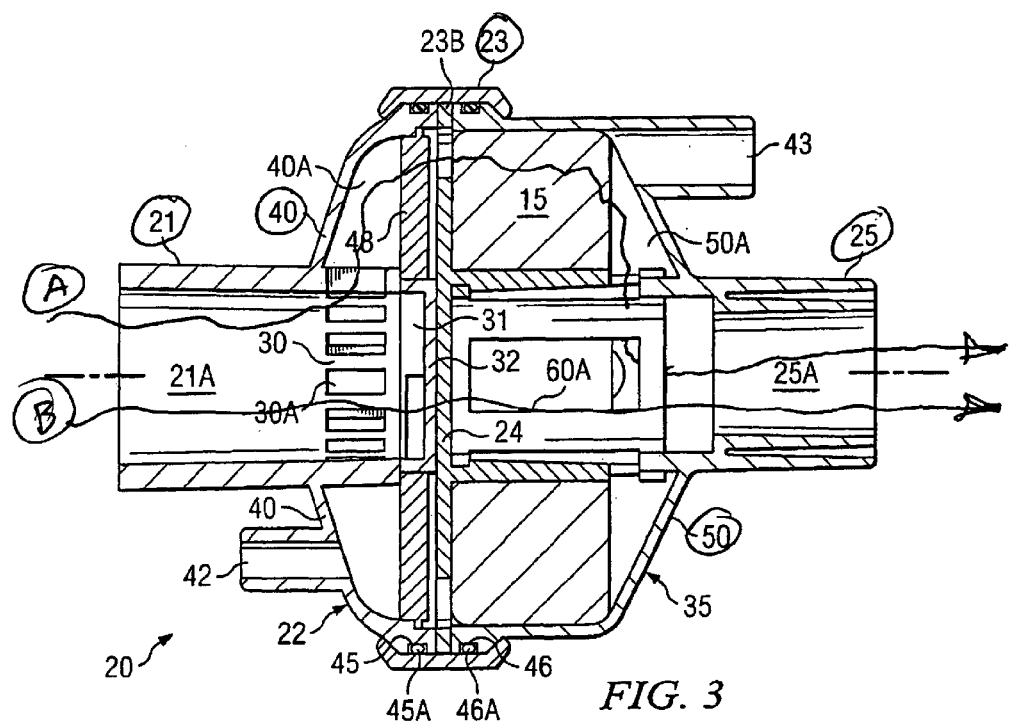
Figure 4:
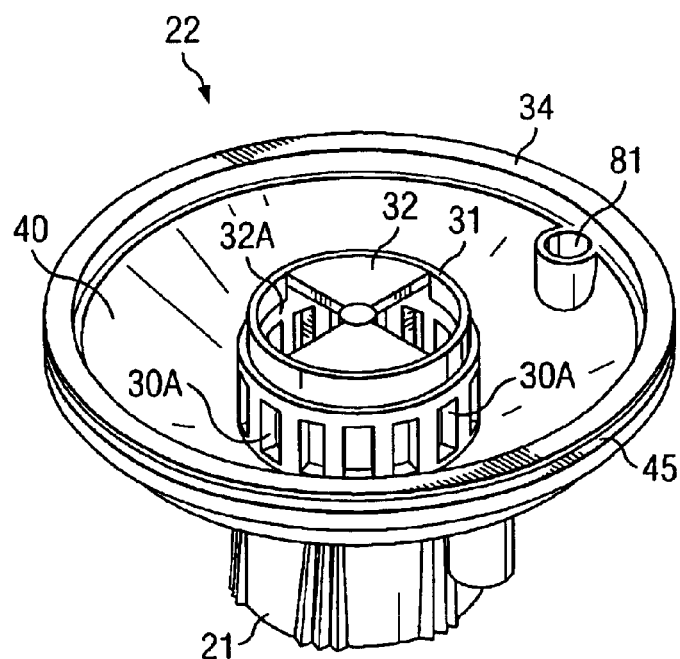

As shown in both FIGS. 3 and 4, the main cylindrical wall of cage 30 has a number of elongated, rectangular, uniformly spaced openings 30A.

Figure 5:
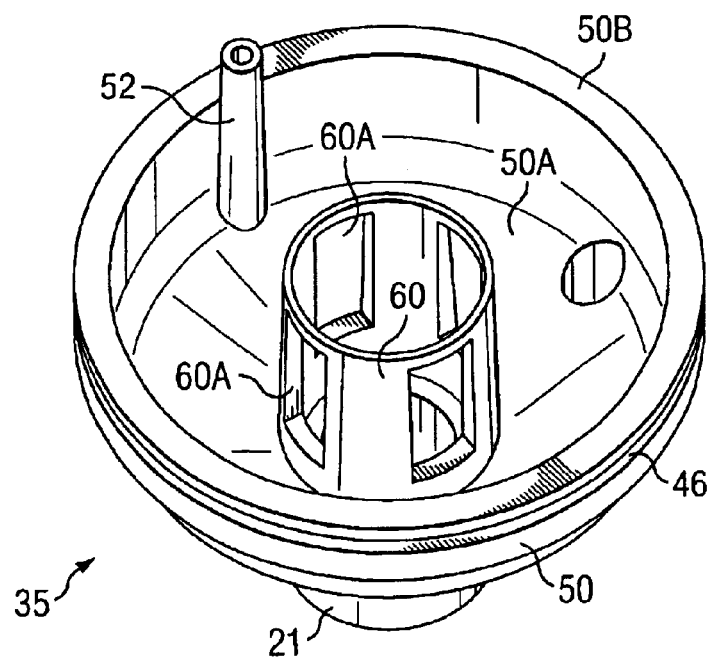
Figure 6:
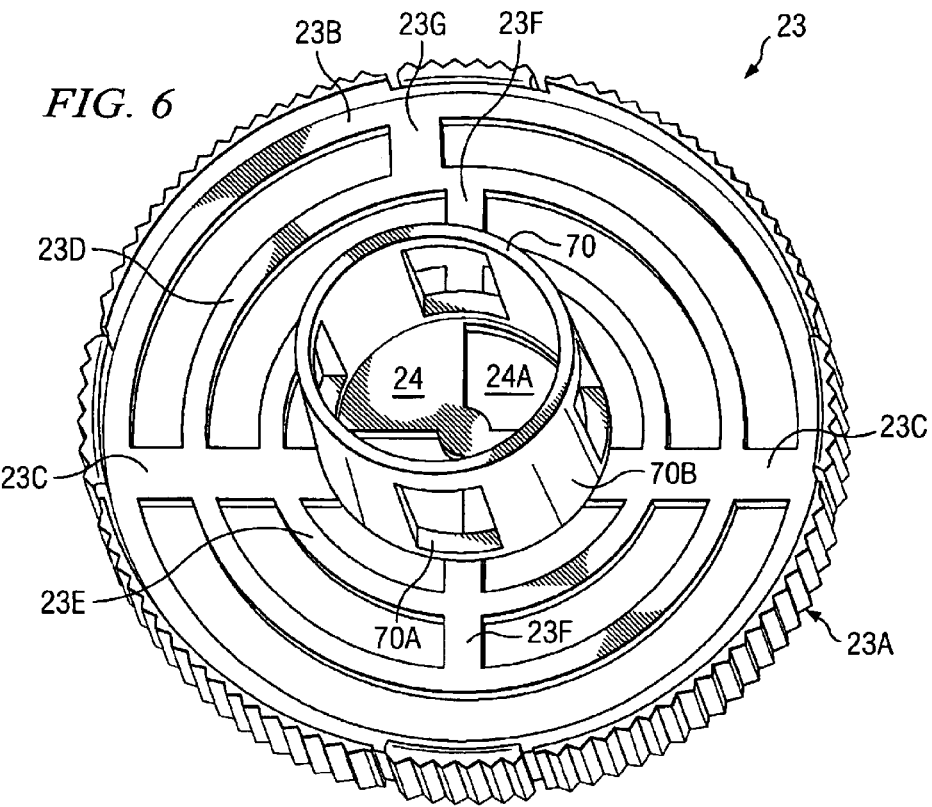
Figure 7:
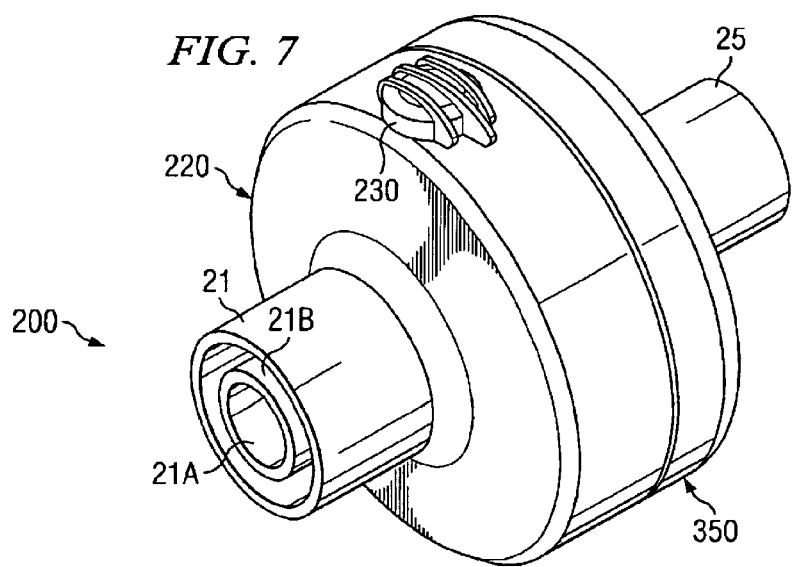

The right peripheral edge of ventilator-side section 22 is bounded by a planar, annular surface 34 (FIG. 4) which abuts and slides against a corresponding annular planar surface of annular ring 23B of valve plate 23, as shown in FIG. 6. An O ring 45A is disposed in a circumferential O ring grove 45 around the outside surface of chamber wall 40 and performs a seal with the inside surface diameter of knurled collar 23A. A receiving boss 81 is positioned on the inside diameter of chamber wall 40 to receive a keying post 52 (FIG. 5) to ensure proper alignment of patient-side section 35 with ventilator-side section 22, annular ring 23B of valve plate 23 being "sandwiched" between annular planar face 34 of ventilator-side section 22 and annular planar surface 50B of patient-side section 35. Keying post 52 also acts as a stop to limit the 90 degree rotation of valve plate 23 in either direction by engaging the portions of spokes 23C and 23G between outer ring 23B (FIG. 6) and middle ring 23D.

The details of valve plate 23 are shown in FIG. 6. Knurled collar 23A surrounds and is rigidly attached to a planar structure including two flat, co-planar, diametrically aligned spokes 23C and two flat, coplanar, diametrically aligned spokes 23F which are perpendicular to spokes 23C. The planar structure also includes three flat, co-planar, concentric, annular rings, including above mentioned outer annular ring 23B, and also includes middle ring 23D and inner ring 23E. Outer ring 23B is rigidly attached to the inner diameter surface of knurled collar 23A, and is connected to the outer end of each of spokes 23C. Middle ring 23D is attached to a mid portion of each of spokes 23C.

The inner end of each of spokes 23C is rigidly attached to opposed portions of the outer cylindrical surface of an outer cage 70. An outer end of each of spokes 23F is attached to and integral with middle ring 23D. The inner end of each of spokes 23F is rigidly attached to opposed portions of the outer cylindrical surface of outer cage 70.

A main cylindrical surface of outer cage 70 (FIG. 6) has therein a plurality of uniformly spaced, elongated openings 70A that can be selectively aligned with or misaligned with openings 60A in inner cage 60 (FIG. 5) in order to either (1) allow air from ventilator 101 (FIG. 2A) to flow through HME element 15 and openings 60A or (2) block openings 60A. The selective alignment or misalignment is achieved by rotating knurled collar 23A through 90 degrees (relative to the complete chamber wall 40,50 with valve plate 23 "sandwiched" between left annular surface 34 and right annular surface 50B). A semi-circular disk 24 covers half of the inner end of outer cage 70. Two sectors of circular disk 24 cover part of the inner end of outer cage 70.

Figure 2:
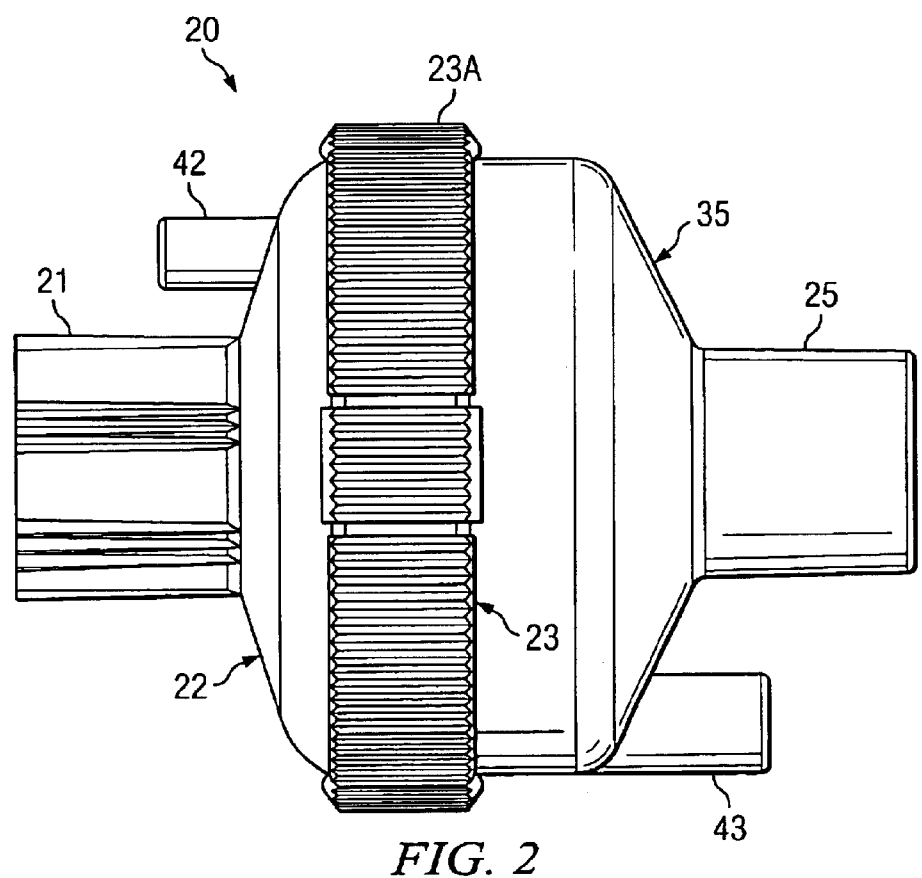
Figure 2A:
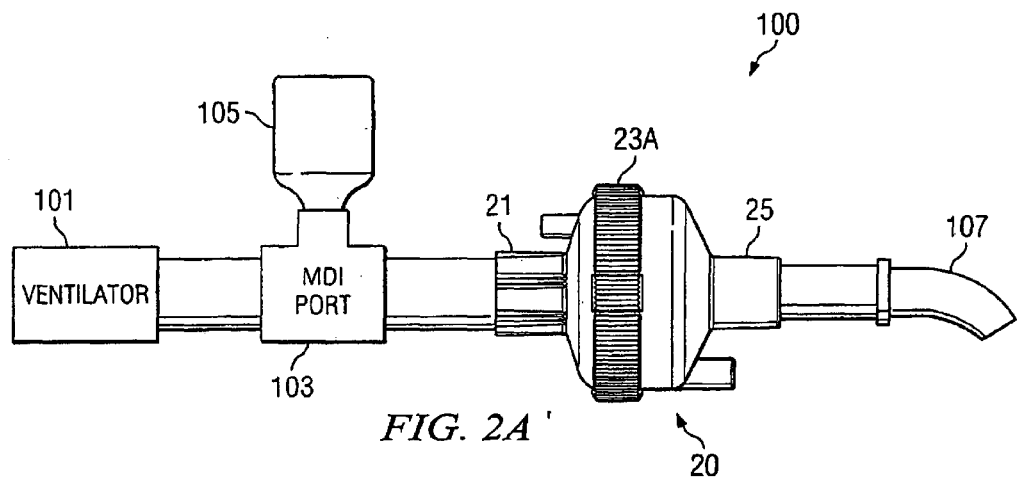

Referring to FIGS. 5 and 6, the inner surface of outer cage 70 of valve plate 23 can slide over the outer surface of inner cage 60 of a ventilator-side section 22 when it, valve plate 23, and patient-side section 35 are assembled into the unitary structure shown in FIGS. 2 and 3. The annular, planar face 50B of patient-side section 35 abuts and slides against the front face of outer ring 23B (FIG. 4), and the keying post 52 attached to the inner surface of right chamber wall 50 of patient-side section 35 extends into the corresponding receiving boss 81 of left chamber wall 40.

A second O ring groove 46 (FIGS. 3 and 5) is circumferentially formed in the outer surface of chamber wall 50, and a second O ring 46A is supported in second O ring groove 46. The first O ring 45A forms a seal between valve plate 23 and ventilator-side section 22, and the second O ring 46A forms a seal between valve plate 23 and patient-side section 35.

Ventilator-side section 22 and patient-side section 35 both will be permanently snapped on to valve plate 23. Preferably, all of the components of HME/bypass device 20 with the exception of the HME element 15 and the optional bacterial and viral filter are composed of suitable plastic, such as clear ABS plastic, acrylic, polycarbonate, or polypropylene.

When valve plate 23 is rotated to a first position such that its two openings 24A are precisely aligned with the two openings 60A of ventilator-side section 22, then semicircular opening 24A adjacent to disk sectors 24 are also precisely aligned with the openings 32A adjacent to disk sectors 32, thereby providing a clear passage from ventilator-side port 21 to patient-side port 25. At the same time, the solid "vanes" 70B of outer cage 70 (FIG. 6) are precisely aligned with openings 60A of inner cage 60, and thereby prevent air carrying aerosolized medication from passing through HME clement 15, optional bacterial and viral filter 48, and openings 60A, so essentially all of the aerosolized medication flows unobstructed through the endotracheal tube 107 into the patient's bronchial passages and lungs.

When valve plate 23 is rotated 90 degrees from the first position to a second position such that its disk sectors 24 are precisely aligned with the openings 32A of ventilator-side section 22, then disk sectors 32 adjacent to openings 32A are also precisely aligned with openings 24A adjacent to disk sectors 24, thereby completely blocking passage of the air from ventilator-side port 21 directly to patient-side port 25 and diverting all of such air from passage 21A through openings 30A of left cage 30 into the first chamber 40A through optional bacterial and viral filter 48, and through the various gaps between rings 23B, 23D and 23E so the air flows into second chamber 50A, through HME element 15 in second chamber 50A, and then through the openings 70A of outer cage 70 and the aligned openings 60A of inner cage 60 and into passage 25A.

Another embodiment of the HME/bypass device of the present invention is shown in FIGS. 7–10. This embodiment has a substantially simpler internal valve structure and an easier-to-use external control for switching between HME operation and bypass operation in which aerosol medication is introduced into the air stream generated by ventilator 101. Where appropriate, the same or similar reference numerals used in FIGS. 2–6 are also used in FIGS. 7–10, sometimes with an added "0". Referring to FIGS. 7–10, HME/bypass device 200 includes a ventilator-side section 220 and a patient-side section 350 that can be press-fit or snap-fit onto ventilator-side section 220. Ventilator-side section 220 has a ventilator-side port 21 having an inlet passage 21A, gas sampling port (not shown, but similar to port 42 of FIG. 2), and two generally cylindrical ventilator hose connecting surfaces, one being the inner surface of ventilator-side port 21 and the other being the outer surface of a smaller-diameter concentric cylindrical tube 21B. A standard ventilator hose for coupling to intubated adults can be connected to the inner surface of port 21, and a smaller ventilator hose for coupling to intubated children can be connected to the outer surface of concentric cylindrical tube 21B. Similarly, a smaller ventilator hose can be coupled to the inner concentric cylindrical tube 25B on patient-side port 25 for coupling to a ventilator circuit adapted for children.

A butterfly valve assembly is mounted axially within the housing formed by ventilator-side housing 400 and patient-side housing 500. The valve assembly, shown in FIGS. 8–10, is supported by six vanes 54 which are integral to the ventilator-side housing 220 and are symmetrically positioned around a gas flow path that is concentric with ventilator-side housing 220.

A cylindrical valve housing 37 is axially supported by the inner edges of the six vanes 54. One or more of the opposed vanes 54 extends between a pair of axial ribs 58, which are integral with the valve housing 37 and which are spaced far enough apart to accommodate the vanes 54. The vanes 54 support valve housing 37 so that the end thereof closest to the wall of ventilator-side housing 220 is spaced from it by a gap 55 through which air from ventilator 101 can flow when the valve is closed, thereby causing the air from ventilator 101 to be diverted around, rather than through the valve housing 37.

A semicircular slot 38 in the upper surface of valve housing 37 is wide enough to allow the planar, semicircular vanes 74 of the butterfly valve and a valve post 78 to which vanes 74 are attached to pass through during assembly. The diameter of the circle formed by the outer edges of the two vanes 74 is slightly less than inside diameter of cylindrical valve housing 37, in order to allow the butterfly valve to be smoothly opened and closed by rotating an actuation knob 230 attached to the upper end of a valve actuation stem 73 having a lower male coupling element 73A which engages a female coupling element 77 attached to the top of valve post 78.

As shown in FIG. 8, HME filter 15 has an annular shape and fits snugly over the outer surface of valve cylinder 37. The outer radial surface of HME filter 15 fits snugly against the inner cylindrical surface of patient-side housing 500. Therefore, when the butterfly valve is closed so that vanes 74 block the inner cylindrical passage through valve cylinder 37, air from ventilator 101 passes through an annular gap 55 and through HME filter 15 before then passing through patient-side port passage 25A and through a suitable ventilator hose to endotracheal tube 107 (FIG. 2). However, if actuation knob 230 is rotated 90 degrees from its closed position so that vanes 74 are parallel to the longitudinal axis of valve cylinder 37, then air from ventilator 101 containing aerosol medication injected from MDI canister 105 into the airstream by means of MDI injection port 103, passes freely through the unrestricted valve cylinder 37 and from there into the intubated patient, without loss of any medication particles that would otherwise be removed by HME filter 15.

The structure of the valve assembly including vanes 74 and valve post 78 is shown in FIG. 10. A flexible snap-on anchor 78A is provided at the bottom of valve post 78, and has an associated slot 78D provided in the lower end of valve post 78 to allow flexing that allows the bottom end of valve post 73 to be snapped into and retained in a hole 41 in the bottom of valve cylinder 37. The bottom of female coupling element 77 limits the depth to which vanes 74 can be passed through slot 38 and an upper hole 44 in valve housing 37. A valve actuator stem 73 extends through O-ring 57 (FIG. 8) and ventilator-side housing 400 with the male coupling element 73A at its base being press fit into an opening 77A in female coupling element 77. O-ring 57 is disposed around actuator stem 73 to provide a rotary seal between stem 73 and the ventilator-side housing 400, and is housed within knob 230 between the inside surface of a boss on the top of ventilator-side housing 400 and actuator stem 73.

Ramp style detents (not shown) are provided on the outer surface of ventilator-side housing 400 to conveniently index control knob 230 to either its "valve closed" or HME position or its "valve open" or bypass position. Preferably, all of the components of HME/bypass device 200, with the exception of the HME element 15 and the optional bacterial and viral filter, are composed of suitable plastic, such as clear ABS plastic, acrylic, polycarbonate, or polypropylene.

HME/bypass device 200 is easily assembled by first inserting the valve mechanism snap fit element 78A through hole 44 and semicircular slot 38 in valve housing 37 until the bottom of female coupling element 77 comes into contact with the outside diameter of valve housing 37. Valve housing 37 is then inserted between the inside edges of the six radial vanes 54 and pressed into position as shown in FIGS. 8 and 9. Actuator stem 73 is subsequently fed through the inside diameter of O-ring 57 and hole 47 in ventilator-side housing 400 with male coupling element 73A being press fit into female coupling element 77. HME element 15 is then placed between the outside surface of valve housing 37 and the inside surface of ventilator-side housing 400, as shown in FIG. 8. Finally, ventilator-side housing 400 is press fit into patient-side housing 500, completing the assembly.

As is the case for the HME/bypass device 20 of FIGS. 1–6, an optional bacterial and viral filter 48 can be provided within HME/bypass device 200, and a gas sampling port 42 and/or a drainage port 43 as shown in FIG. 3 also can be provided for HME/bypass device 200.

The described HME/bypass devices have far smaller "dead space" than the bypass tube 8 of the prior art CIRCUVENT device 4 shown in FIG. 1. The described HME/bypass devices, especially HME/bypass device 200, are much smaller, lighter, less expensive, and easier to use than the combination of the prior art CIRCUVENT device with an HME device or HME device connected thereto. The cost of manufacture of HME/bypass device 200 is expected to be only slightly higher than the cost of prior HME devices alone, and much lower than the total cost of the prior art CIRCUVENT device in combination with a conventional HME device connected therein as shown in FIG. 1.

While the invention has been described with reference to several particular embodiments thereof, those skilled in the art will be able to make the various modifications to the described embodiments of the invention without departing from the true spirit and scope of the invention. It is intended that all elements or steps which are insubstantially different or perform substantially the same function in substantially the same way to achieve the same result as what is claimed are within the scope of the invention.

What is claimed is:

1. A heat and moisture exchanger for selectively conducting a stream of air produced by a ventilator through a moisturizing medium or causing the stream of air to bypass the moisturizing medium, the heat and moisture exchanger comprising:

(a) a housing having a ventilator-side port configured to be coupled to an outlet of a ventilator and a source of aerosolized medication, the housing also having a patient-side port configured to be coupled to a patient to provide ventilation to the patient;

(b) a structure within the housing forming a first path within the housing for conducting non-aerosolized air from the ventilator-side port through the moisturizing medium to the patient-side port and a second path within the housing for conducting air carrying aerosolized medication from the ventilator-side port to the patient-side port by bypassing the moisturizing medium; and (c) a two-way valve mechanism in the housing for selectively coupling the ventilator-side port into fluid communication with one or the other of the first and second paths.

2. The heat and moisture exchanger of claim 1 including an external valve control extending through the housing for controlling the two-way valve mechanism.

3. The heat and moisture exchanger of claim 2 wherein the structure includes a tube located between the ventilator-side port and the patient-side port, the second path extending entirely through the tube, wherein the two-way valve mechanism selectively blocks or opens a portion of the second path extending through the tube in response to the external valve control, the moisturizing medium being disposed between an outer surface of the tube and an inner surface of the housing, the first path extending around the tube and through the moisturizing medium.

4. The heat and moisture exchanger of claim 3 including a gap between a first end of the tube and the ventilator-side port, the gap forming part of the first path.

5. The heat and moisture exchanger of claim 3 wherein the two-way valve mechanism includes a valve post having an upper end portion extending through the housing and attached to the external valve control and a lower end portion extending through a wall of the tube, and wherein the two-way valve mechanism also includes a butterfly valve vane located in the tube and attached to the lower end portion of the valve post.

6. The heat and moisture exchanger of claim 5 wherein the tube includes an elongated slot for admitting the valve post and the butterfly valve vane.

7. The heat and moisture exchanger of claim 3 wherein the moisturizing medium is annular and is disposed around the tube, an inner surface of the moisturizing medium forming a seal with an outer surface of the tube, an outer surface of the moisturizing medium forming a seal with an inner surface of the housing.

8. The heat and moisture exchanger of claim 7 wherein the tube and the housing are cylindrical, and wherein the inner surface and outer surface of the moisturizing medium are cylindrical.

9. The heat and moisture exchanger of claim 3 wherein the housing includes a ventilator-side section and a patient-side section which are fit together as a unit to form the housing.

10. The heat and moisture exchanger of claim 3 wherein the ventilator-side section includes a plurality of integral support members which support the tube in axial alignment between the ventilator-side port and the patient-side port.

11. The heat and moisture exchanger of claim 4 wherein the first end of the tube extends beyond the two-way valve mechanism toward the ventilator-side port, the housing forming a volume within which an antibacterial and viral filter can be disposed in the first path.

12. The heat and moisture exchanger of claim 1 including a gas sampling port for providing fluid communication with the interior of the housing.

13. A method for conducting a stream of air produced by a ventilator through a moisturizing medium contained within a heat and moisture exchanger and selectively bypassing the moisturizing medium to conduct aerosolized medication in the stream from a ventilator-side port of the heat and moisture exchanger through a patient-side port thereof, the method comprising:

(a) providing an internal bypass path within the heat and moisture exchanger to bypass the moisturizing medium;

(b) providing a two-way valve within the heat and moisture exchanger to selectively block the internal bypass path;

(c) operating an external valve control to cause the two-way valve to open the internal bypass path;

(d) introducing medication particles into the stream of air produced by the ventilator to produce aerosolized medication in the stream, wherein the stream flows from the ventilator-side port through the internal bypass path and the patient-side port; and (e) after the aerosolized medication has passed through the patient-side port, operating the external valve control to cause the two-way valve to block the internal bypass path, wherein the stream of air produced by the ventilator flows from the ventilator-side port through the moisturizing medium and the patient-side port.

* * * * *